(12) United States Patent
Judd et al.

(10) Patent No.: US 10,047,128 B2
(45) Date of Patent: Aug. 14, 2018

(54) ENCRYPTION OF ADENO-ASSOCIATED VIRUSES WITH ENZYMATICALLY DECODED PEPTIDE LOCKS

(71) Applicant: WILLIAM MARSH RICE UNIVERSITY, Houston, TX (US)

(72) Inventors: Justin Judd, Houston, TX (US); Junghae Suh, Houston, TX (US); Jonathan Silberg, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 417 days.

(21) Appl. No.: 13/872,949

(22) Filed: Apr. 29, 2013

(65) Prior Publication Data

US 2013/0330766 A1    Dec. 12, 2013

Related U.S. Application Data

(60) Provisional application No. 61/639,818, filed on Apr. 27, 2012.

(51) Int. Cl.
*C07K 14/005* (2006.01)

(52) U.S. Cl.
CPC ........ *C07K 14/005* (2013.01); *C07K 2319/33* (2013.01); *C07K 2319/50* (2013.01); *C12N 2750/14122* (2013.01); *C12N 2750/14145* (2013.01); *C12N 2810/40* (2013.01)

(58) Field of Classification Search
None
See application file for complete search history.

(56) References Cited

U.S. PATENT DOCUMENTS

2012/0009268 A1* 1/2012 Asokan et al. ............... 424/499

OTHER PUBLICATIONS

Kridel et al., Substrate Hydrolysis by Matrix Metalloproteinase-9, 2001, Journal of Biological Chemistry, vol. 276, No. 23, pp. 20572-20578.*

* cited by examiner

*Primary Examiner* — Benjamin P Blumel
(74) *Attorney, Agent, or Firm* — Reed Smith LLP; Robert R. Riddle; Matthew S. Gibson

(57) ABSTRACT

The present invention is a peptide lock that comprises at least one peptide that is genetically encoded into the Adeno-associated virus (AAV) capsid that block biologically active domains on the virus capsid surface. The peptide lock, can be processed by biological enzymes to restore biological behavior of the capsid-displayed domains, thus 'decoding the lock' or opening the lock. A method of forming the peptide lock comprises providing at least one peptide, providing an Adeno-associated virus capsid and genetically inserting the at least one peptide into the Adeno-associated virus capsid to block the biologically active domains on the virus capsid surface.

22 Claims, 13 Drawing Sheets

Non-target Cells

Target Cells
(Breast Cancer)

MOI: 10,000
TPI: 24h

MOI: 10,000
TPI: 24h

MOI: 10,000
TPI: 24h

Figure 8(a)

| Site | Lock Peptide Sequence | Name | Titer* |
|---|---|---|---|
| 453 | AG-PLGLAR-G-DDDD-G-PLGLAR-GA (SEQ ID NO: 3) | 453-PAV | ◊◊◊ |
| 586 | AG-PLGLAR-G-DDDD-G-PLGLAR-GA (SEQ ID NO: 3) | 586-PAV | ◊◊◊ |
| 586 | AGG-PLGLAR-G-DDDD-G-PLGLAR-GGA (SEQ ID NO: 13) | 586-PAV-G2 | ◊◊◊ |
| 586 | AGGG-PLGLAR-G-DDDD-G-PLGLAR-GGGA (SEQ ID NO: 14) | 586-PAV-G3 | ◊◊◊ |
| 587 | AG-PLGLAR-G-DDDD-G-PLGLAR-GA (SEQ ID NO: 3) | 587-PAV | ◊◊◊ |
| 587 | AGG-PLGLAR-G-DDDD-G-PLGLAR-GGA (SEQ ID NO: 15) | 587-PAV-G2 | ◊◊◊ |
| 587 | AGGG-PLGLAR-G-DDDD-G-PLGLAR-GGGA (SEQ ID NO: 14) | 587-PAV-G3 | ◊◊◊ |
| 590 | AG-PLGLAR-G-DDDD-G-PLGLAR-GA (SEQ ID NO: 3) | 590-PAV | ◊◊◊ |
| 586 | AG-PLGLAR-G-KKKK-G-PLGLAR-GA (SEQ ID NO: 16) | 586-2OR7-K4 | ◊ |
| 586 | AG-PLGLAR-G-SGGS-G-PLGLAR-GA (SEQ ID NO: 17) | 586-2OR7-SGGS | ◊◊ |
| 586 | AG-PLGLAR-G-AAAA-G-PLGLAR-GA (SEQ ID NO: 18) | 586-2OR7-A4 | ◊◊ |
| 586 | AG-GPQGIAGQ-G-DDDD-G-GPQGIAGQ-GA (SEQ ID NO: 19) | 586-PAV-v1 | ◊◊◊ |
| 586 | AG-IPESLRAG-G-DDDD-G-IPESLRAG-GA (SEQ ID NO: 5) | 586-PAV-v2 | ◊◊◊ |
| 586 | AG-IPVSLRSG-G-DDDD-G-IPVSLRSG-GA (SEQ ID NO: 6) | 586-PAV-v3 | ◊◊◊ |
| 586 | AG-RPFSMIMG-G-DDDD-G-RPFSMIMG-GA (SEQ ID NO: 20) | 586-PAV-v4 | ◊ |
| 586 | AG-VPLSLTMG-G-DDDD-G-VPLSLTMG-GA (SEQ ID NO: 21) | 586-PAV-v5 | ◊◊◊ |
| 586 | AG-VPLSLYSG-G-DDDD-G-VPLSLYSG-GA (SEQ ID NO: 22) | 586-PAV-v6 | ◊◊◊ |
| 586 | AG-VPMSMRGG-G-DDDD-G-VPMSMRGG-GA (SEQ ID NO: 7) | 586-PAV-v7 | ◊◊◊ |
| 586 | AG-PLGLWAR-G-DDDD-G-PLGLWAR-GA (SEQ ID NO: 23) | 586-PAV-W | ◊ |
| 586 | AG-HPGGPQ-G-DDDD-G-HPGGPQ-GA (SEQ ID NO: 24) | 586-PAV-CTSK | ◊◊◊ |
| 586 | AG-HPGGPQ-G-DDDD-G-PLGLAR-GA (SEQ ID NO: 25) | 586-CTSK-AND-MMP-D4 | ◊◊◊ |
| 586 | AG-PLGLAR-G-DDDD-G-HPGGPQ-GA (SEQ ID NO: 26) | 586-MMP-AND-CTSK-D4 | ◊◊◊ |

NLQR⁵⁸⁵G-AG-PLG↓LAR-G-DDDD-G-PLG↓LAR-GA-NR⁵⁸⁸QAA

A₄: AAAA

SG₂S: SGGS

SEQUENCE LISTING

<160> NUMBER OF SEQ ID NOS: 26

<210> SEQ ID NO 1
<211> LENGTH: 6

```
<212> TYPE: PRT
<213> ORGANISM: Artificial Sequence
<220> FEATURE:
<223> OTHER INFORMATION: enzymatically processable motif

<400> SEQUENCE: 1

Pro Leu Gly Leu Ala Arg
1               5

<210> SEQ ID NO 2
<211> LENGTH: 5
<212> TYPE: PRT
<213> ORGANISM: Artificial Sequence
<220> FEATURE:
<223> OTHER INFORMATION: linker

<400> SEQUENCE: 2

Gly Gly Gly Gly Ser
1               5

<210> SEQ ID NO 3
<211> LENGTH: 22
<212> TYPE: PRT
<213> ORGANISM: Artificial Sequence
<220> FEATURE:
<223> OTHER INFORMATION: peptide lock

<400> SEQUENCE: 3

Ala Gly Pro Leu Gly Leu Ala Arg Gly Asp Asp Asp Gly Pro Leu
1               5                   10                  15

Gly Leu Ala Arg Gly Ala
            20

<210> SEQ ID NO 4
<211> LENGTH: 4
<212> TYPE: PRT
<213> ORGANISM: Artificial Sequence
<220> FEATURE:
<223> OTHER INFORMATION: inactivating peptide

<400> SEQUENCE: 4

Asp Asp Asp Asp
1

<210> SEQ ID NO 5
<211> LENGTH: 26
<212> TYPE: PRT
<213> ORGANISM: Artificial Sequence
<220> FEATURE:
<223> OTHER INFORMATION: peptide lock

<400> SEQUENCE: 5

Ala Gly Ile Pro Glu Ser Leu Arg Ala Gly Gly Asp Asp Asp Gly
1               5                   10                  15

Ile Pro Glu Ser Leu Arg Ala Gly Gly Ala
            20                  25

<210> SEQ ID NO 6
<211> LENGTH: 26
<212> TYPE: PRT
<213> ORGANISM: Artificial Sequence
<220> FEATURE:
<223> OTHER INFORMATION: peptide lock

<400> SEQUENCE: 6

Ala Gly Ile Pro Val Ser Leu Arg Ser Gly Gly Asp Asp Asp Gly
```

```
                1               5                   10                  15
Ile Pro Val Ser Leu Arg Ser Gly Gly Ala
            20                  25
```

<210> SEQ ID NO 7
<211> LENGTH: 26
<212> TYPE: PRT
<213> ORGANISM: Artificial Sequence
<220> FEATURE:
<223> OTHER INFORMATION: peptide lock

<400> SEQUENCE: 7

```
Ala Gly Val Pro Met Ser Met Arg Gly Gly Gly Asp Asp Asp Gly
1               5                   10                  15
Val Pro Met Ser Met Arg Gly Gly Gly Ala
            20                  25
```

<210> SEQ ID NO 8
<211> LENGTH: 6
<212> TYPE: PRT
<213> ORGANISM: Artificial Sequence
<220> FEATURE:
<223> OTHER INFORMATION: enzymatically processable motif

<400> SEQUENCE: 8

```
His Pro Gly Gly Pro Gln
1               5
```

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
aggaccaggc ctcatacatc tc                                              22

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgtccaaggc agccttgatt                                                 20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
tcacggggat ttccaagtct c                                               21

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
aatggggcgg agttgttacg ac 22

<210> SEQ ID NO 13
<211> LENGTH: 24
<212> TYPE: PRT
<213> ORGANISM: Artificial Sequence
<220> FEATURE:
<223> OTHER INFORMATION: peptide lock

<400> SEQUENCE: 13

Ala Gly Gly Pro Leu Gly Leu Ala Arg Gly Asp Asp Asp Gly Pro
1               5                   10                  15

Leu Gly Leu Ala Arg Gly Gly Ala
            20

<210> SEQ ID NO 14
<211> LENGTH: 26
<212> TYPE: PRT
<213> ORGANISM: Artificial Sequence
<220> FEATURE:
<223> OTHER INFORMATION: peptide lock

<400> SEQUENCE: 14

Ala Gly Gly Gly Pro Leu Gly Leu Ala Arg Gly Asp Asp Asp Gly
1               5                   10                  15

Pro Leu Gly Leu Ala Arg Gly Gly Gly Ala
            20                  25

<210> SEQ ID NO 15
<211> LENGTH: 24
<212> TYPE: PRT
<213> ORGANISM: Artificial Sequence
<220> FEATURE:
<223> OTHER INFORMATION: peptide lock

<400> SEQUENCE: 15

Ala Gly Gly Pro Leu Gly Leu Ala Arg Gly Asp Asp Asp Gly Pro
1               5                   10                  15

Leu Gly Leu Ala Arg Gly Gly Ala
            20

<210> SEQ ID NO 16
<211> LENGTH: 22
<212> TYPE: PRT
<213> ORGANISM: Artificial Sequence
<220> FEATURE:
<223> OTHER INFORMATION: peptide lock

<400> SEQUENCE: 16

Ala Gly Pro Leu Gly Leu Ala Arg Gly Lys Lys Lys Lys Gly Pro Leu
1               5                   10                  15

Gly Leu Ala Arg Gly Ala
            20

<210> SEQ ID NO 17
<211> LENGTH: 22
<212> TYPE: PRT
<213> ORGANISM: Artificial Sequence
<220> FEATURE:
<223> OTHER INFORMATION: peptide lock

<400> SEQUENCE: 17

Ala Gly Pro Leu Gly Leu Ala Arg Gly Ser Gly Gly Ser Gly Pro Leu
1               5                   10                  15

Gly Leu Ala Arg Gly Ala
            20

<210> SEQ ID NO 18
<211> LENGTH: 22
<212> TYPE: PRT
<213> ORGANISM: Artificial Sequence
<220> FEATURE:
<223> OTHER INFORMATION: peptide lock

<400> SEQUENCE: 18

Ala Gly Pro Leu Gly Leu Ala Arg Gly Ala Ala Ala Ala Gly Pro Leu
1               5                   10                  15

Gly Leu Ala Arg Gly Ala
            20

<210> SEQ ID NO 19
<211> LENGTH: 26
<212> TYPE: PRT
<213> ORGANISM: Artificial Sequence
<220> FEATURE:
<223> OTHER INFORMATION: peptide lock

<400> SEQUENCE: 19

Ala Gly Gly Pro Gln Gly Ile Ala Gly Gln Gly Asp Asp Asp Gly
1               5                   10                  15

Gly Pro Gln Gly Ile Ala Gly Gln Gly Ala
            20                  25

<210> SEQ ID NO 20
<211> LENGTH: 26
<212> TYPE: PRT
<213> ORGANISM: Artificial Sequence
<220> FEATURE:
<223> OTHER INFORMATION: peptide lock

<400> SEQUENCE: 20

Ala Gly Arg Pro Phe Ser Met Ile Met Gly Gly Asp Asp Asp Gly
1               5                   10                  15

Arg Pro Phe Ser Met Ile Met Gly Gly Ala
            20                  25

<210> SEQ ID NO 21
<211> LENGTH: 26
<212> TYPE: PRT
<213> ORGANISM: Artificial Sequence
<220> FEATURE:
<223> OTHER INFORMATION: peptide lock

<400> SEQUENCE: 21

Ala Gly Val Pro Leu Ser Leu Thr Met Gly Gly Asp Asp Asp Gly
1               5                   10                  15

Val Pro Leu Ser Leu Thr Met Gly Gly Ala
            20                  25

<210> SEQ ID NO 22
<211> LENGTH: 24
<212> TYPE: PRT
<213> ORGANISM: Artificial Sequence
<220> FEATURE:
<223> OTHER INFORMATION: peptide lock

<400> SEQUENCE: 22

Ala Gly Pro Leu Gly Leu Trp Ala Arg Gly Asp Asp Asp Asp Gly Pro

```
                1               5                   10                  15
Leu Gly Leu Trp Ala Arg Gly Ala
            20

<210> SEQ ID NO 23
<211> LENGTH: 24
<212> TYPE: PRT
<213> ORGANISM: Artificial Sequence
<220> FEATURE:
<223> OTHER INFORMATION: peptide lock

<400> SEQUENCE: 23

Ala Gly Pro Leu Gly Leu Trp Ala Arg Gly Asp Asp Asp Gly Pro
1               5                   10                  15
Leu Gly Leu Trp Ala Arg Gly Ala
            20

<210> SEQ ID NO 24
<211> LENGTH: 22
<212> TYPE: PRT
<213> ORGANISM: Artificial Sequence
<220> FEATURE:
<223> OTHER INFORMATION: peptide lock

<400> SEQUENCE: 24

Ala Gly His Pro Gly Gly Pro Gln Gly Asp Asp Asp Gly His Pro
1               5                   10                  15
Gly Gly Pro Gln Gly Ala
            20

<210> SEQ ID NO 25
<211> LENGTH: 22
<212> TYPE: PRT
<213> ORGANISM: Artificial Sequence
<220> FEATURE:
<223> OTHER INFORMATION: peptide lock

<400> SEQUENCE: 25

Ala Gly His Pro Gly Gly Pro Gln Gly Asp Asp Asp Gly Pro Leu
1               5                   10                  15
Gly Leu Ala Arg Gly Ala
            20

<210> SEQ ID NO 26
<211> LENGTH: 22
<212> TYPE: PRT
<213> ORGANISM: Artificial Sequence
<220> FEATURE:
<223> OTHER INFORMATION: peptide lock

<400> SEQUENCE: 26

Ala Gly Pro Leu Gly Leu Ala Arg Gly Asp Asp Asp Gly His Pro
1               5                   10                  15
Gly Gly Pro Gln Gly Ala
            20
```

ENCRYPTION OF ADENO-ASSOCIATED VIRUSES WITH ENZYMATICALLY DECODED PEPTIDE LOCKS

CROSS-REFERENCE TO RELATED APPLICATIONS

This application claims priority to U.S. Provisional Application No. 61/639,818, filed Apr. 27, 2012, which is incorporated by reference.

This disclosure includes a sequence listing submitted as a text file pursuant to 37 C.F.R. § 1.52(e)(v) named 13-21051-US ST25.txt, created on Aug. 12, 2013, with a size of 8 kilobytes, which is incorporated herein by reference. The attached sequence descriptions and Sequence Listing comply with the rules governing nucleotide and/or amino acid sequence disclosures in patent applications as set forth in 37 C.F.R. §§1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984). The symbols and format used for nucleotide and amino acid sequence data comply with the rules set forth in 37 C.F.R. §1.822.

STATEMENT OF GOVERNMENT INTEREST

This invention was made with government support under Grant Number DMR-0955536 awarded by National Science Foundation and Grant Number T32 GM008362 awarded by National Institutes of Health. The U.S. government has certain rights in the invention.

BACKGROUND

Adeno-associated viruses (AAVs) are small viruses which infect humans and some other primate species. AAVs are not currently known to cause disease and consequently the viruses cause a very mild immune response. Gene therapy vectors using AAV can infect both dividing and non-dividing cells and persist in an extrachromosomal state without integrating into the genome of the host cell. These features make AAVs very attractive candidates for creating viral vectors for gene therapy, and for the creation of isogenic human disease models.

SUMMARY

Embodiments of this disclosure are described throughout the specification and are not limited to this brief summary.

The present disclosure generally relates to Adeno-associated virus platforms.

In one embodiment, the present disclosure provides a device comprising one or more peptides genetically encoded into an AAV capsid, wherein the one or more peptides block biologically active domains on the virus capsid surface.

In certain embodiments, the device comprises one or more peptides genetically encoded into an AAV capsid to form a "peptide lock," wherein the one or more peptides block biologically active domains on the virus capsid surface.

In one aspect, the present device is an enzyme-processable Adeno-associated virus (AAV) vector.

In yet another aspect, the present device is an enzyme-activatable Adeno-associated virus (AAV) vector.

In one aspect, the present device is a protease-activatable Adeno-associated virus vector or protease-activatable virus (PAV).

In other embodiments, the properties and characteristics of the PAV are modified to generate PAVs variants with altered sensitivity and specificity that are activatable by different types of proteases.

The features and advantages of the present disclosure will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

Figure 8B:
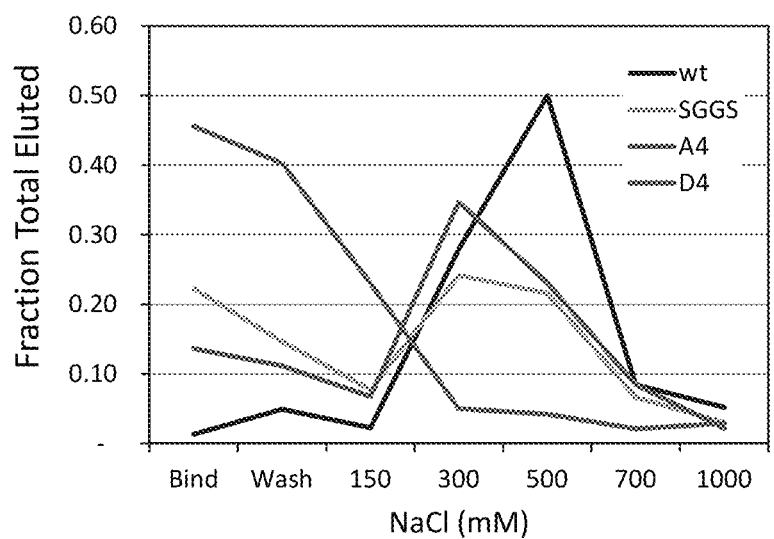
FIG. 8(a) is a chart depicting variations of the Peptide Lock.

FIG. 8(b) is a graph and drawing that depicts the role of the $D_4$ motif in the peptide lock. The $D_4$ motif in the protease-activatable virus embodied in the "586-PAV" (shown below graph) was mutated to alanines ($A_4$) or SGGS ($SG_2S$) to determine the role of the negatively charged $D_4$ motif in blocking AAV-receptor interactions. The 586-PAV containing the $D_4$ motif shows low affinity for heparin, with peak elution in bind and wash fractions. The neutral charged A4 and $SG_2S$ mutations resulted in partial recovery of heparin affinity, evidenced by peak fractions at higher salt, closer to wt.

Figure 9:
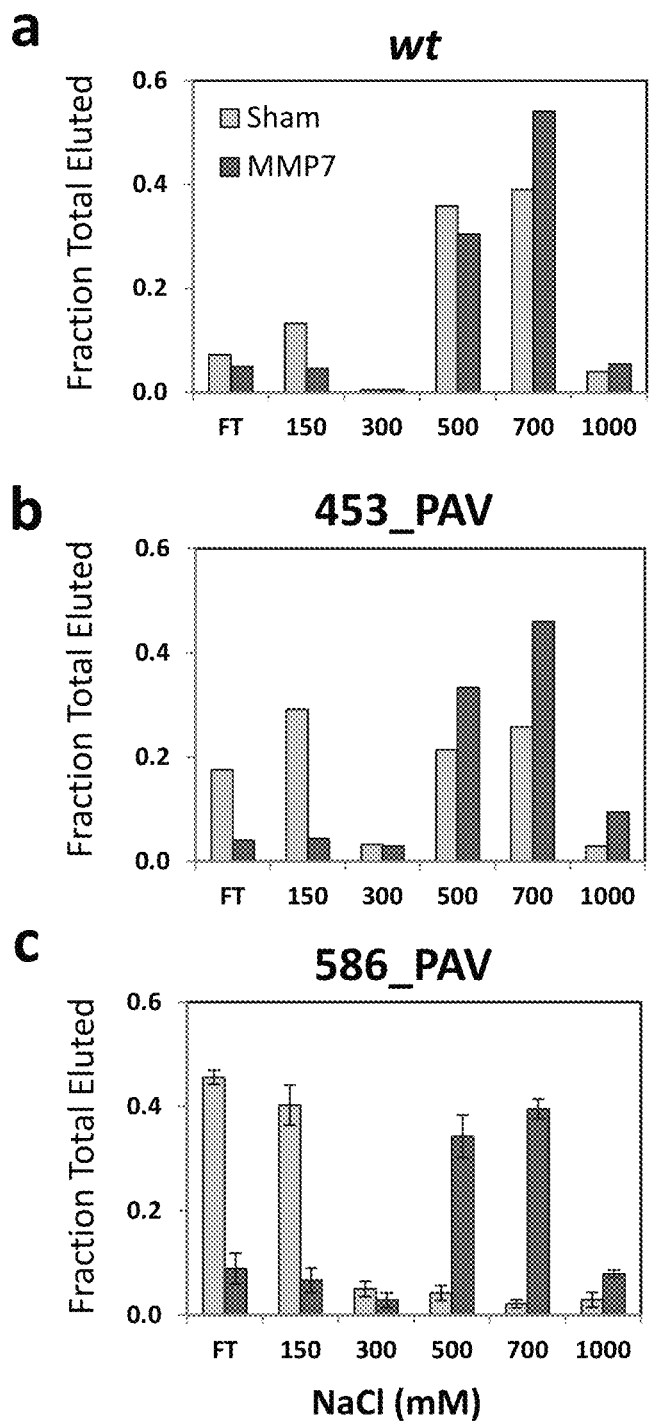

FIG. 9 is a drawing that illustrates protease-activatable receptor binding by protease-activatable virus ("PAV") with a peptide lock or a "PAV lock." (a) wt AAV elutes from heparin affinity column in high salt after treatment with MMP7 (red bars) or a sham buffer (grey bars), indicating it retains high affinity for its primary receptor independent of treatment condition; (b) 453-PAV behaves similarly to wt, with elution peaks at high salt under either condition; (c) 586-PAV displays protease activatable receptor binding, as it has low affinity until it is treated with MMP7.

Figure 10:
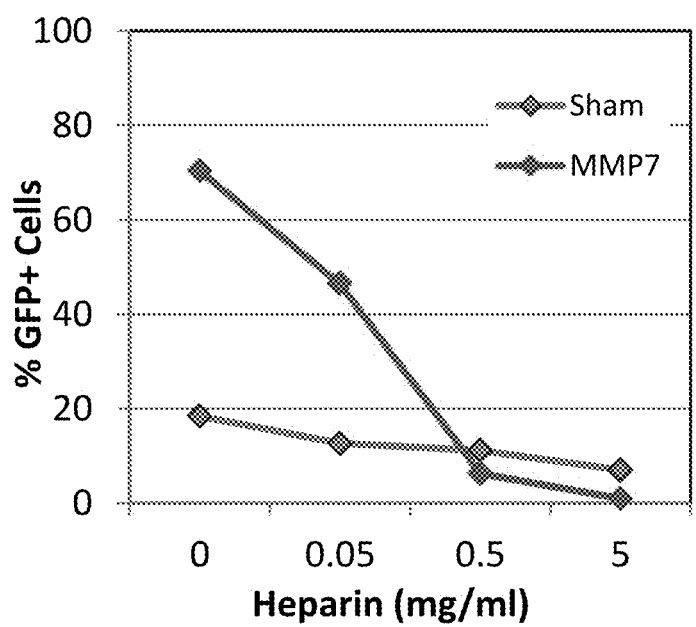

FIG. 10 is a drawing that illustrates that protease-activatable cell transduction by 586-PAV is heparin dependent.

Figure 11:
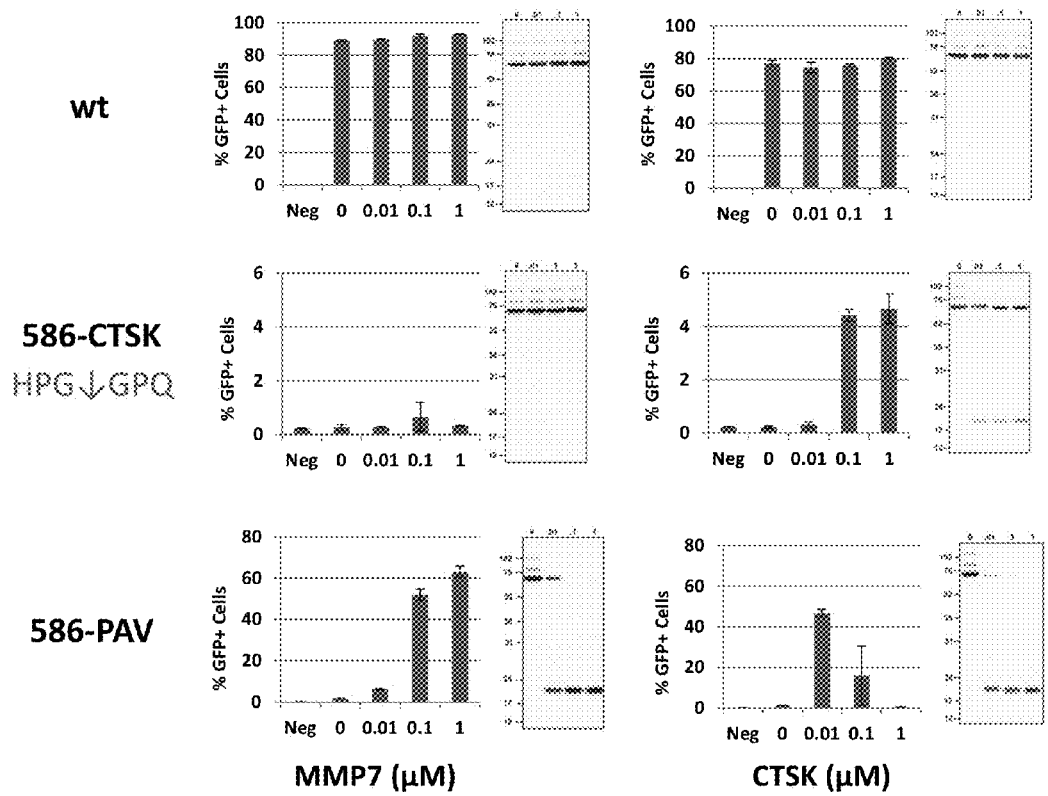

FIG. 11 graphs illustrating the sensitivity and specificity of one embodiment of the PAV, the 586-PAV, and a variant of the 586-PAV called the 586-PAV-CTSK. Transfer functions were generated by treating the viruses with increasing concentrations of MMP7 (left column) or CTSK (right column) for 4 hours at 37° C. before applying to monolayer of 293T cells. Western blots are shown at the right of each graph, indicating the degree of cleavage at each treatment level. As expected, the wt capsid is not affected by any treatment level, whereas the 586-PAV mutant increases gene expression dose-dependently in response to MMP7 treatment, plateauing around 100 nM recombinant MMP7. The 586-PAV mutant also responds to CTSK, but appears to behave in a bandpass fashion, where transduction is knocked down at higher concentrations. Replacement of the proteolytic linkers yields an AAV vector (586-PAV-CTSK) with altered specificity that does not respond to MMP7, but does respond to CTSK. However, the efficiency is lower than that of the 586-PAV variant.

Figure 12:
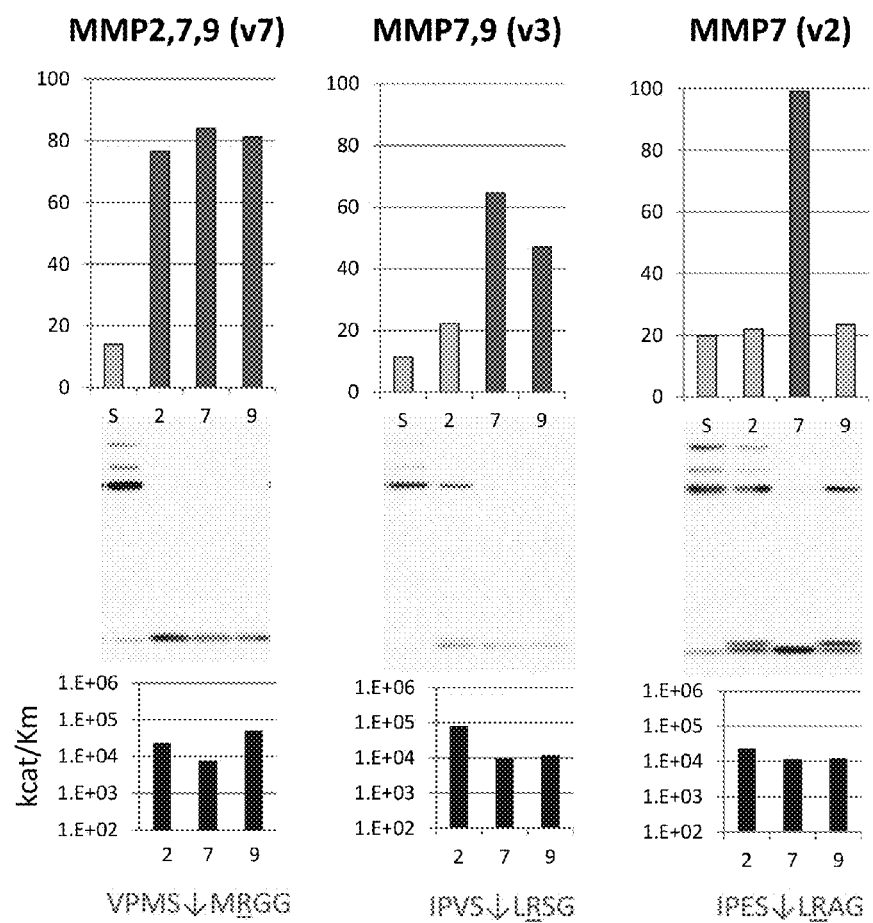

FIG. 12 are graphs showing the results from tuning the specificity of PAV variants with alternate cleavage motifs. PAV variants were designed by replacing the cleavage domains in the prototype PAV lock at position 586. Variants were found that exhibit altered specificity with respect to MMPs 2, 7 and 9. v2 was specific only for MMP7 and exhibited the highest efficiency of any PAV tested after activation. The lock design is shown at bottom, where the cleavage domain is represented by XXXX↓XXXX (red lettering, arrow indicates scissile bond), and the capsid residues indicated by grey letters. The critical heparin binding residues R585 and 588 are labeled. The cleavage sequence of each variant is shown below in red; arginine (R) residues, potentially involved in restoring heparin binding after cleavage are underlined. Western blots in the middle show the cleavage patterns of the PAV locks by each enzyme. Note there is a negative correlation between incomplete digestion (indicated by double bands and full length VPs) and PAV activation.

Figure 13:
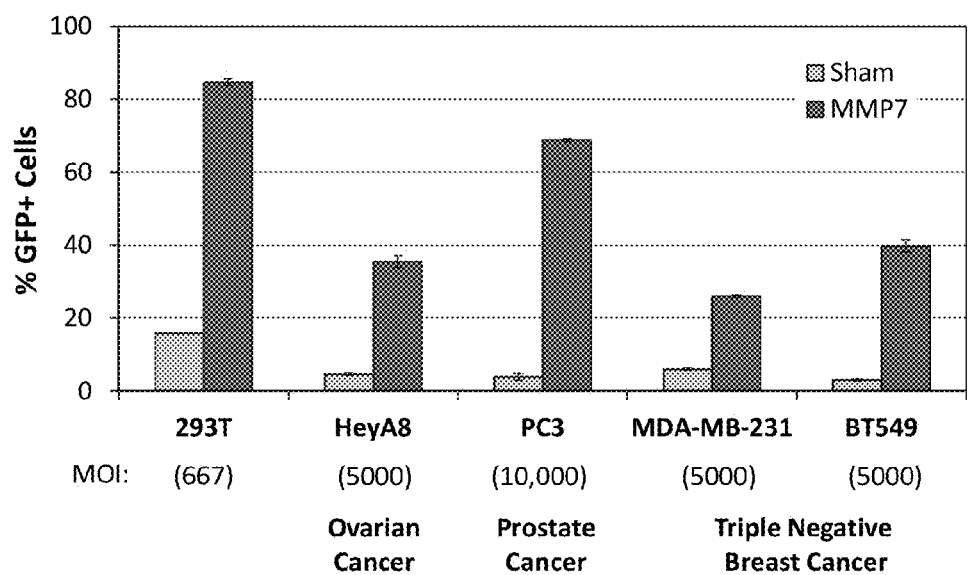

FIG. 13 is a graph depicting the protease-controlled transduction in clinically relevant cancer model cell lines. 586-PAV was treated with MMP7 or a sham condition and then applied to cell lines modeling ovarian (HeyA8), prostate (PC3), and triple-negative breast (MDA-MB-231 and BT549) cancer. MOIs are indicated below. MMP7 treatment drastically increases the transduction efficiency in each cell line.

Figure 14:
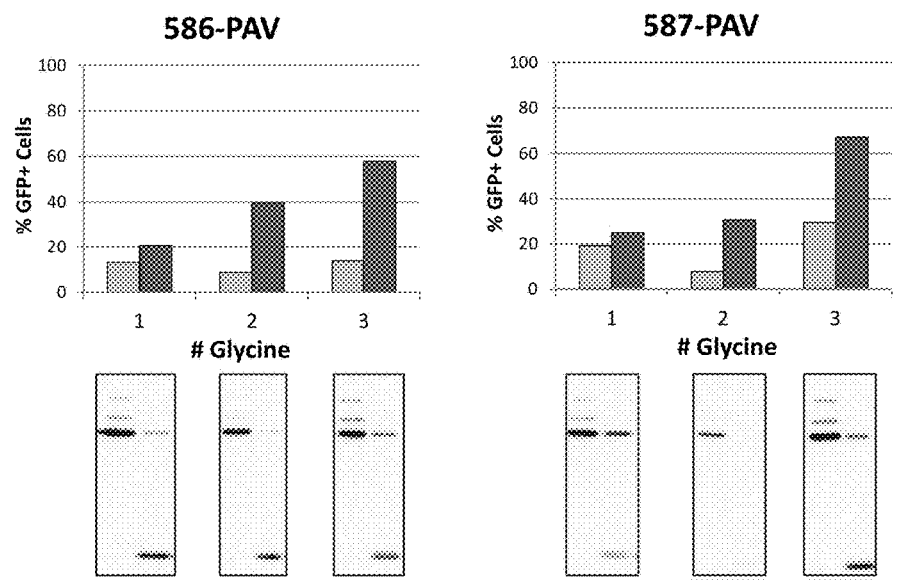
Figure 14:
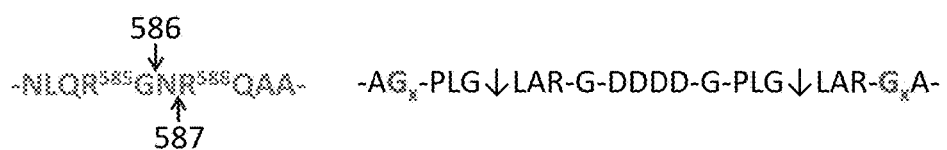

FIG. 14 depicts the effect of glycine linker length PAV lock susceptibility to MMP2. The prototypic PAV lock used in the in vivo work contains one linker at the indicated position (red text in sequence at right below). Variants were created containing 2 or 3 glycines at this position and in with the PAV lock inserted at either position 586 or 587 as indicated below. Viruses were treated with 100 nM MMP-2 or a sham and then applied to 293T cells at MOI=1000. Flow cytometry was used to quantify the number of transduced cells at 60 hours post-transduction. As seen in the graphs above, MMP-2 cleavage is activation improved by increasing glycine linker length, suggesting a role for steric access.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure may be embodied in other specific forms without departing from its essential characteristics. The described embodiments are to be considered in all respects only as illustrative and not as restrictive.

As described, defined, and set forth herein, it is to be understood that the terms "peptide device" "peptide lock" and "device" are being used interchangeably in the present disclosure.

The present disclosure generally relates to Adeno-associated virus platforms. In contrast to previously developed enzyme-activated retroviruses, Adeno-associated virus platforms may pose significantly lower health risks during production and clinical use. The peptide locks of the present disclosure may be targeted to enzymatic, soluble biomarkers of disease. Previous work in AAV targeting has been based on receptor-ligand interactions and genetic regulation of transgene expression, once the gene has been delivered. The peptide locks and methods of the present disclosure may be used with conventional AAV targeting schemes to improve the specificity of gene delivery to diseased tissues which are characterized by combinations of various enzymatic inputs including, but not limited to many forms of cancer.

In one embodiment, the present disclosure provides a device comprising one or more peptides genetically encoded into an AAV capsid, wherein the one or more peptides block biologically active domains on the virus capsid surface.

In certain embodiments, the device comprises one or more peptides genetically encoded into an AAV capsid to form a "peptide lock," wherein the one or more peptides block biologically active domains on the virus capsid surface.

Figure 1:
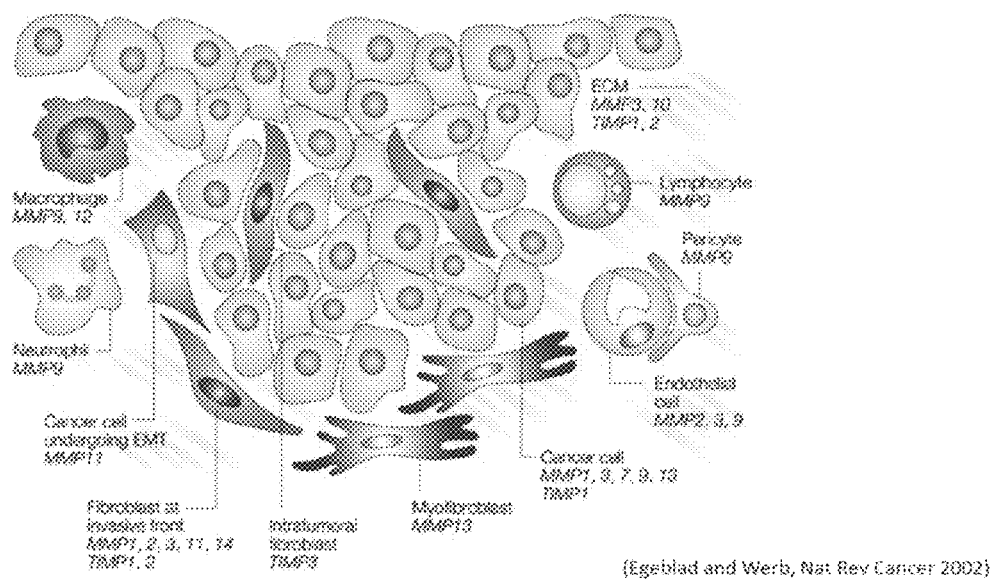
FIG. 1 is drawing that illustrates the expression of matrix metalloproteinases in breast cancer.
Figure 2:
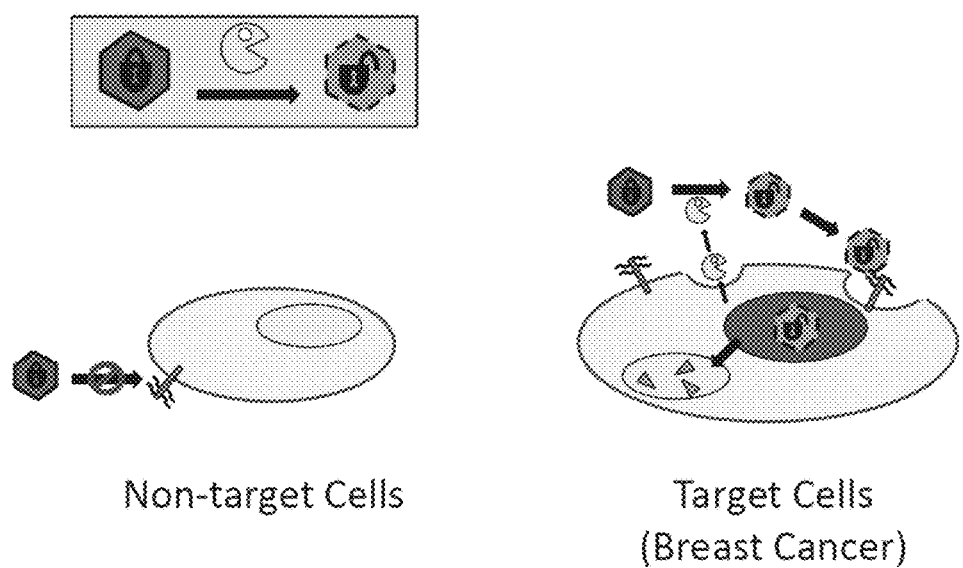
FIG. 2 is a drawing that relates to MMP-Activatable Virus Nanoparticles.

One advantage of the devices discussed herein is that they have the potential to improve AAV specificity by targeting the virion to tissues that express activating enzymes. One non-limiting example of this may be the targeting of the virus to tumors that express the matrix metalloproteinases MMP-7 or MMP-2. For example, and as shown in FIG. 1, matrix metalloproteinases are expressed in breast cancer. Even higher specificity may be gained by requiring multiple inputs to activate the virus via multiple different biologically active outputs that allow the virus to traverse the infection pathway.

Peptide Locks

In one embodiment, the present disclosure provides a device that comprises peptides genetically encoded into the Adeno-associated virus (AAV) capsid that blocks biologically active domains on the virus capsid surface. In certain embodiments, the device comprises one or more peptides genetically encoded into an AAV capsid to form a "peptide lock," wherein the one or more peptides block biologically active domains on the virus capsid surface.

These peptide devices, or peptide locks, can be processed by biological enzymes to restore biological behavior of the capsid-displayed domains, thus 'decoding the lock' or opening the lock.

The peptide locks may be genetically inserted into any of the many available Adeno-associated virus capsid versions, such as Adeno-associated virus 2 (AAV2) and its mutant variants, or alternate serotypes (including but not limited to Adeno-associated virus 1) and their mutant variants. In certain embodiments, the peptide locks may be comprised of at least 1 motif, i.e. an "enzymatically processable" motif that confers the decodable behavior. These may include, but are not limited to protease cleavage domains, such as the peptide sequence 'PLGLAR' (SEQ ID NO: 1). Other enzymatically processable motifs may be used such as peptides that can be modified by other proteases or altogether different enzymes with different modifying behavior. Different enzymes may include, but are not limited to kinases and phosphatases.

Additionally, unlike previous enzyme-activated retroviruses, in certain embodiments, the peptide devices may use endopeptidyl insertion, such that the peptide lock may be anchored by an N- and C-terminus. This allows the encryption of peptide locks that require two enzymatic inputs upstream and downstream of a biologically 'inactivating motif'. This property may confer higher specificity to each lock by allowing the requirement of multiple enzymatic inputs to decode the lock.

In some embodiments, the peptide lock may or may not need additional motifs in order to exhibit the desired behavior. For example, the peptide lock may require a biologically "inactivating motif" flanked by two enzymatically processable motifs.

In additional embodiments, the biologically "inactivating motif" and the enzymatically processable motifs may be separated by linker sequences comprised of peptide sequences of variable length and variable identity, including but not limited to flexible linkers such as 'AG', 'GA', 'G', and 'GGGGS' (SEQ ID NO: 2).

In yet other embodiments, the inactivating motif may be comprised of charged residues that interact electrostatically with oppositely charged domains on the virus capsid, thereby blocking biological activity of the active domain on the virus capsid.

In another aspect of the disclosure, inactivating motifs may include but are not limited to peptides which occlude active domains through sterics and may require forces such as Van der Waals, hydrogen bonding, hydrophobic effects, or specific ligand affinity interactions. In further embodiments, motifs such as unnatural amino acids or biotin-acceptor peptides that can be post-translationally modified with chemical moieties such as PEG, may be used to modulate the activity of biologically active domains on the virus capsid.

Additionally, the peptide locks discussed herein may comprise variations that require multiple inputs to activate the virus. For example, two or more enzyme processing motifs in the peptide lock may be activatable or cleavable by two more types of enzymes. In further embodiments, the two or more enzymes may be a subset of the same class of enzymes. A representative class of enzyme is proteases. Other classes include kinases, and phosphatases. In yet further embodiments, the two or more enzymes may be a subset of a family of enzymes. A representative family of enzymes is matrix metalloproteinases.

In certain embodiments, the peptide lock may require just one of a class or family of enzymatic inputs to activate and may be referred to as an 'OR' logic gate. In some embodiments, the peptide lock may require two enzymatic inputs to activate that may not necessarily be from the same class or family of enzymes. This variation on the peptide lock may be described as an 'OR-AND' logic gate.

In further embodiments, different versions of the peptide lock device may be arranged by combining motifs in varying arrangements. Additionally, multiple peptide locks may be arranged on the capsid surface to achieve higher levels of encryption, such as but not limited to the following. For example, a peptide lock A may be encoded on the virus capsid such that it blocks and regulates access to another peptide lock B, such that lock A must be decoded in to expose lock B for processing. Alternatively, locks A and B may operate independently such that they can be decoded in any order. Furthermore, greater numbers of different locks may be genetically encoded onto the capsid surface to achieve various types and levels of encryption with variable decoding requirements. In yet another embodiment, the peptide locks can be combined with the insertion or mutation of capsid sequences that alter the native tropism, receptor binding and/or binding to non-biological material including but not limited to gold and nickel surfaces.

In yet another embodiment of the peptide lock device, the placement of enzymatically cleavable sequences in some positions may allow enzymatically modulatable conformational changes that facilitate behavior such as the externalization of the otherwise hidden N-terminus or the disassembly of the virus, which may or may not involve the interaction with host cell proteins. In the case of N-terminal externalization, the device can further be modified by encoding various biologically active domains on the N-terminus.

In yet another embodiment, the enzyme-activatable virus comprises nanoparticles. In certain embodiments, the enzyme-activatable virus is a nanoparticle.

In certain embodiments, after a peptide lock is conceived, it may be genetically encoded into a plasmid containing the desired AAV cap gene. The cap genes may be expressed in virus producer cells along with transgene delivery constructs that allow modular packaging of genetic deliverables into the virus capsid, as well as a helper plasmid containing genes that help the virus replicate. The virus can be purified from the producer cells using an array of purification techniques such as density gradient separation and chromatography and other techniques known in the art. Additionally, directed evolution can be performed by creating libraries of viruses containing millions of different variants on the device in a combinatorial fashion, followed by selection for those variants exhibiting desired behavior.

Protease-Activatable AAV Vector

In one embodiment, the device is a protease-activatable Adeno-associated virus (AAV) vector or protease-activatable virus (PAV) with a peptide lock or a "PAV lock."

In certain embodiments, the PAV lock is comprised of at least one tetra-aspartic acid motif ($D_4$), which interferes with electrostatic interactions of negatively charged cell surface glycoproteins, including the primary host cell surface receptor, heparan sulfate proteoglycans (HSPGs.) As shown in FIGS. 8(*a*) and 8(*b*), the role of the $D_4$ motif in AAV-heparin interruption was studied by insertion of the motif into certain residues in the AAV2 capsid; the $D_4$ motif shows low affinity for heparin, indicating that the $D_4$ motif blocks or interferes electrostatically with HSPGs.

In a further aspect of this embodiment, the $D_4$ motif is flanked by proteolytic cleavage motifs, connected by a flexible glycine on each side. In certain embodiments, the peptide lock contains NgoM IV and Kas I RE sites, which encode small amino acids including but not limited to glycine and alanine.

In some embodiments the lock is inserted near a biological receptor-binding domain of the AAV vector.

One non-limiting example of a 'peptide lock' is a mutant 586-D4-20R7 or "586-PAV" which may be formed as follows. A peptide, 'AG-PLGLAR-G-DDDD-G-PLGLAR-GA' (SEQ ID NO: 3) is genetically inserted into the AAV2 capsid after residue 586 (VP1 numbering). This particular example of a peptide lock is comprised of seven motifs in the following order in the primary amino acid sequence: (1) linker 'AG', (2) enzymatically processable motif 'PLGLAR' (SEQ ID NO: 1), cleavable by matrix metalloproteinases MMP-2 or MMP-7 (a subset of protease enzymes) (3) linker 'G', (4) inactivating peptide 'DDDD' (SEQ ID NO: 4), (5) linker 'G, (6) enzymatically processable motif 'PLGLAR' (SEQ ID NO: 1), and (7) linker 'GA'. FIG. 3 shows an embodiment of this peptide lock. This device has been shown to behave as a peptide lock in the following manner. Before processing with enzymatic input MMP-7, the virus has low affinity for its primary cell surface receptor, HSPGs as shown in FIG. 9 and was demonstrated to have low transduction efficiency in 5 different cell lines. FIG. 4 shows an embodiment of the protease-activated (MMP-7) switching of heparin binding behavior. After processing by MMP-7, 586-D4-20R7 binds heparin with high affinity and has increased transduction efficiency on all of the same 5 cell lines, with a peak increase of over an order of magnitude greater number of GFP-positive cells in 293T cells. These results are summarized in the non-limiting embodiments shown in FIGS. 5-7, and 10.

In some embodiments, the mutant 586-D$_4$-2OR7 peptide lock or 586-PAV may be referred to as an "'OR' logic gate," since it can be activated by either MMP-2 or MMP-7 proteases.

In further embodiments the PAV is activated by MMP-7 protease concentration in an amount of about between 0.01 and 0.1 µM and is shown in FIG. 11.

In certain embodiments, the mutant 586-D$_4$-2OR7 peptide lock may be altered to fine tune its activity and response by altering its primary sequence including but not limited to the following: altering the length, identity, and/or placement of any or all of the motifs.

In some embodiments, variants of the 586-PAV were made by replacing or substituting the cleavage domain of the 586-PAV. In certain embodiments, variants of the 586-PAV exhibited altered specificity with respect to MMPs 2, 7, and 9. In one embodiment 586-PAV variant 2 is the peptide AG-IPESLRAG-G-DDDD-G-IPESLRAG-GA (SEQ ID NO: 5). In another embodiment 586-PAV variant 3 is the peptide AG-IPVSLRSG-G-DDDD-G-IPVSLRSG-GA (SEQ ID NO: 6). In yet another embodiment 586-PAV variant 7 is the peptide AG-VPMSMRGG-G-DDDD-G-VPMSMRGG-GA (SEQ ID NO: 7). In certain further embodiments 586-PAV variant 2 ("v2") exhibited specific and saturated transduction upon activation by MMP-7 as shown in FIG. 12. In additional embodiments, 586-PAV variant 3 ("v3") exhibited moderate specificity for MMPs 7 and 9 and low specificity for MMP-2 and as shown in FIG. 12. In yet another embodiment 586-PAV variant 7 ("v7") exhibited high transduction efficiency after activation for each of the proteases tested, MMPs 2, 7, and 9 as shown in FIG. 12.

In some embodiments, the mutant 586-D4-2OR7 peptide lock 'AG-PLGLAR-G-DDDD-G-PLGLAR-GA' (SEQ ID NO: 6) is genetically inserted into the AAV2 capsid after residue 586 with extra glycines in the linkers that connect the peptide lock with the native capsid sequence. As shown in FIG. 14, increasing the glycine linker increased the cleavage efficiency and transduction ability of the mutant 586-D4-2OR7 peptide lock by the MMP-2 protease. In additional embodiments, extra glycines were added to the linker motifs of the peptide lock amino acid sequence for insertion into other residues in the AAV2 capsid.

Additionally, the peptide locks discussed herein may comprise variations that require multiple inputs to activate the virus. For example, replacement of one 'PLGLAR' motif in the 586-D4-2OR7 mutant with a sequence cleavable by a different enzyme such as, but not limited to 1-1PGGPQ' (SEQ ID NO: 8), which is cleavable by a different type of protease Cathepsin K (CTSK) is possible. This device may then require two enzymatic inputs in order to activate, i.e. both MMP-7 and CTSK or both MMP-2 and CTSK. This variation on the peptide lock may be described as an 'OR-AND' logic gate.

In yet other embodiments, different versions of the protease-activatable virus (PAV) or PAV peptide lock device may be arranged by combining motifs in varying arrangements. In certain embodiments, multiple protease activatable peptide locks may be arranged on the capsid surface to achieve higher levels of encryption, such as but not limited to the following. For example, a peptide lock A may be encoded on the virus capsid such that it blocks and regulates access to another peptide lock B, such that lock A must be decoded in order to expose lock B for processing. In this example, the peptide lock A may be activated by only a certain class or family of proteases and peptide lock B can only be activated by different class or family of proteases. In alternative embodiments, locks A and B may operate independently such that they can be decoded in any order. In further embodiments, greater numbers of different locks may be genetically encoded onto the capsid surface to achieve various types and levels of encryption with variable decoding requirements that are specific to the various classes and families of proteases.

In certain embodiments, the multiple peptide locks may be activated by a combination of proteases and other types of enzymes, including but not limited to kinases and phosphatases. In yet another embodiment, the protease activated peptide locks can be combined with the insertion or mutation of capsid sequences that alter the native tropism, receptor binding and/or binding to non-biological material including but not limited to gold and nickel surfaces.

In some embodiments, the 586-$D_4$-20R7 peptide lock is activated by moderate levels of CTSK. In further embodiments the PAV is activated by CTSK in an amount of about between 0.01 and 0.1 μM as shown in FIG. 11.

In yet another embodiment, the protease-activatable virus comprises nanoparticles. In further embodiments, the matrix metalloproteinases (MMP)-activatable virus comprises nanoparticles. In certain embodiments, the protease-activatable virus is a nanoparticle. In some embodiments, the MMP-activatable virus is a nanoparticle as shown in FIG. 2.

EXAMPLES

Materials and Methods

Plasmids.

pRepCap was created by subcloning the AAV genome (without ITRs) from pSub201 into a pBlueScript SK II (+) backbone using Xba I. The plasmid vector was then subjected to site-directed mutagenesis to remove existing Kas I, NgoM IV, Nco I and BfuA I (RaPID restriction sites) restriction sites with silent mutations. The VP3 start codon was mutagenized to produce a Nco I site and a BfuA I site was inserted just downstream of the stop codon, yielding pRepCap_RR (RR: RaPID ready). The modified genome was then subcloned into pSub201ΔNgoMIV (pSub201 with the NgoM IV site removed from the vector backbone) using Xba I sites to regain the ITRs, yielding pSub201_RR. To create the pAAV2_RR expression vector, the entire modified genome (with ITRs) was then cut from pSub201_RR using Pvu II, and ligated to the pET28a(+) backbone between the Pvu II and Xmn I sites. To generate pAAV2_RRΔcap, pSub201_RR was digested with BsiW I and Xcm I, blunted with T4 DNA polymerase and religated. The partially deleted cap gene was then subcloned into pAAV2_RR using Nco I and BfuA I sites. pMIN_VP3 was created by excising VP3 from pRepCap_RR using Nco I and BfuA I sites, and ligating to a minimized plasmid backbone generated by sequence overlap extension[155] using pBAD24 as a template. pInSALect_RR was created by removal of RaPID restriction sites from pInSALect, followed by insertion of Nco I and BfuA I sites between the intein sequences. Mosaic expression vectors were constructed as previously described. Briefly, pAAV2_RR was mutagenized to knock out the major splice acceptor site downstream of the VP1 start codon, giving VP1-only expression vector pAAV2_VP1_RR. For wt VP2/VP3 expression, pRC_RR was mutagenized to knock out the VP1 start codon, yielding pRC_RR_VP2/3.

RaPID Library Construction.

pMIN_VP3 was digested with dilute DNase I (New England Biolabs, Ipswich, Mass.) in 1 mM MnCl2, resulting in a pool of randomly linearized plasmids. This pool was resolved by agarose gel electrophoresis with a restriction endonuclease (RE) linearized control to identify the near-full length linearized fraction, which was excised and purified using a Zymoclean Gel DNA recovery kit (Zymo Research, Irvine, Calif.). The randomly linearized pool was then blunted with T4 DNA polymerase and dephosphorylated with T4 Polynucleotide Kinase (NEB). The mCherry ORF was amplified by sequence overlap extension to remove Nco I and Kas I sites and to add an NgoM IV site upstream and a Kas I site downstream of the coding sequence. Pfu DNA polymerase was used for mCherry amplification to generate blunt ends, allowing ligation to the linearized pool of cap genes. Transformation into DH10β E. coli (Life Technologies, Grand island, N.Y.) was followed by amplification on agar plates, and purification using a Zyppy Plasmid Miniprep Kit (Zymo Research). The resulting plasmid library was then size-selected by agarose gel electrophoresis to enrich the single insert-containing fraction. The size selected naïve pool was then subcloned into pInSALect_RR using Nco I and BfuA I restriction sites, followed by three rounds of selection on agar containing carbenicillin (100 µg/ml) and chloramphenicol (50 µg/ml). The frame-selected plasmid pool was purified and the mutant cap genes were subcloned into pAAV2 RRΔcap using Nco I and BfuA I sites to create pAAV2 RaPID. The VP1 only library, pAAV2 VP1 RaPID was created by cloning the VP3 library from pAAV2 RaPID into VP1-only expression vector pAAV2_VP1 RRΔcap using Nco I and BfuA I.

Virus Production.

The AAV2 RaPID_mCherry virus libraries were generated by linear polyethyleneimine-mediated (MW 25 kD) triple transfection of pAAV2_VP1_RaPID_mCherry (10 ng), pRC_RR_VP2/3 (5 µg), and pXX6 (25 µg) into each of 10×15 cm poly-L-lysine-coated plates of 70% confluent 293T. The cells were harvested 46-48 hours post-transfection, lysed by 3 cycles of freeze/thaw in 1% protease inhibitor cocktail (Sigma-Aldrich, St. Louis, Mo.) and treated with 4 U/ml Benzonase (Sigma-Aldrich) for 30 min. The lysate was then clarified by centrifugation and loaded onto an iodixanol step gradient (15/25/40/54%) in Beckman Ultra-Clear QuickSeal Tubes (Beckman Coulter, Brea, Calif.). The lysate was resolved by centrifugation at 48,000 RPM for 1.75 hours in a 70Ti rotor, and the purified virus library extracted from the 40% layer. The genomic titer was determined by quantitative PCR (qPCR) using SYBR green (Life Technologies) and primers against rep (FW: AGGAC-CAGGCCTCATACATCTC (SEQ ID NO: 9), RV: TGTC-CAAGGCAGCCTTGATT (SEQ ID NO: 10)) on a BIO-RAD CFX96. Clonal production of r1c3 packaged with its genome for TEM studies was performed similarly using pAAV2_VP1_RaPID_r1c3 (2 pmol), pRC_RR_VP2/3 (2 pmol), and XX6 (2 pmol). For confocal and transduction studies, r1c3 was packaged with a GFP transgene. Its genome was cloned into pBlueScript SK II (+) using Xba I to remove ITRs, generating pRC_RR_VP1 r1c3. 293T cells were then transfected as above with pRC_RR_VP1_r1c3 (1 pmol), pRC_RR_VP2/3 (1 pmol), pAAV_GFP (containing a CMV-GFP reporter flanked by AAV2 ITRs) (1 pmol), and XX6 (1.65 pmol) and purified as above. Virus titers were quantified via qPCR using primers against the CMV promoter in the GFP transgene cassette (FW: TCACGGGGATTTCCAAGTCTC (SEQ ID NO: 11), RV: AATGGGGCGGAGTTGTTACGAC (SEQ ID NO: 12)).

Virus Selection.

The virus library was applied to 70% confluent 293T cells at a multiplicity of infection (MOI) of approximately 10 viral genomes per cell. 4 hours after infection, the library was rescued with adenovirus serotype 5 at an MOI of approximately 10 IU/cell (IU: infectious units). 48 hours post-infection, the cells were harvested by trypsinization, pelleted and resuspended in PBS (5 mM EDTA). The cells were then filtered through a 40 µM cell strainer (BD, Franklin Lakes, N.J.) and sorted using a Dako MoFlo cell sorter. mCherry positive cells were lysed by 3 cycles of freeze/thaw and purified using a Zyppy Plasmid Miniprep Kit after adding 1 µg of salmon sperm DNA as a carrier. Cap genes were amplified by PCR using a Roche Expand Hi-Fidelity PCR kit (Roche, Indianapolis, Ind.) and subcloned into pAAV2_VP1_RRΔcap using Nco I and BfuA I.

Western Blot.

Virus samples were resolved in 4-12% or 12% Bis-Tris NuPAGE gels (Life Technologies) and transferred to nitrocellulose (GE Healthcare, Pittsburgh, Pa.) at 40V for 90 minutes, otherwise following manufacturer guidelines. Gels were run under reducing conditions, except for the heparin fractions. Blocking was performed in 5% skim milk in PBS with 0.1% Tween-20 (PBS-T) for 1 hour while rocking. To wash, blots were rinsed 3 times and rocked for 20 minutes in PBS-T. Primary antibodies were applied to blots overnight at 4° C. in PBS with 3% BSA (3% BSA-PBS) at the following dilutions. A1 (monoclonal mouse anti-VP1 from American Research Products, Belmont, Mass.) was diluted 1:200; B1 (monoclonal mouse anti-VP1,2,3 from ARP) diluted 1:50; and mCherry (polyclonal rabbit from BioVision, Milpitas, Calif.) diluted 1:100. After washing, goat anti-mouse (Jackson ImmunoResearch, West Grove, Pa.) or rat anti-rabbit (ARP) peroxidase-conjugated secondary antibodies were applied at a 1:2000 dilution in 5% skim milk in PBS-T for 1 hour. Blots were then washed 4 times for 15 minutes with PBS-T while rocking Imaging was performed on a Fujifilm LAS 4000 after applying Lumi-Light western blotting substrate (Roche).

Immunoelectron Microscopy.

Purified virus samples were applied to charged carbon grids (Ted Pella, Redding, Calif.) for 5 min; wt was adsorbed to a 300 mesh grid with lacey carbon type-A (Product No. 01890-F), while r1c3 was applied to a 300 mesh grid with continuous carbon (Product No. 01753-F). Grids were then blocked for 45 min with 3% BSA-PBS, washed in 3 drops of PBS and stained with the polyclonal anti-mCherry antibody (see above) for 1 hour. After washing, gold nanoparticle (12 nm) conjugated goat anti-rabbit secondary antibodies (Jackson ImmunoResearch) were applied at a 1:30 dilution in 3% BSA-PBS for 1 hour to visualize mCherry proteins attached to the virions. Samples were then washed and negative stained with 0.75% uranyl formate to highlight the viral capsids before imaging on a JEOL 2010 transmission electron microscope operating at 120 kV.

Heparin Chromatography.

Virus samples were applied to a HiTrap heparin-sepharose column (GE Healthcare) equilibrated with 50 mM Tris-Cl, pH 7.6, 10 mM MgCl2, and 150 mM NaCl. Fractionation was performed by passing increasing concentrations of NaCl in 1 ml increments and collecting the flow-through. Fractions were quantified by qPCR or analyzed by western blot as above.

Confocal Microscopy.

HeLa cells were seeded onto poly-L-lysine-coated glass coverslips in a 24-well tissue culture plate at a density of $6 \times 10^4$ cells per well in phenol-red free DMEM supplemented with 10% fetal bovine serum and 1% penicillin-streptomycin. The following day, r1c3-GFP was applied in serum-free media for 6 hours at 37° C., 5% CO2. Cells were then washed twice with PBS, fixed in 4% paraformaldehyde for 15 minutes, washed twice and stained with DAPI (1 µg/ml) for 15 minutes. After washing twice more in PBS, cells were mounted onto glass slides in 5 µl of Fluoromount-G (SouthernBiotech, Birmingham, Ala.). Samples were allowed to dry at 4° C. overnight before examination on a Zeiss LSM 710. Images were processed using Zen 2010 software.

Transduction Assay.

HeLa cells were seeded at $1 \times 10^5$ cells per well in a PLL-coated 24-well tissue culture plate and incubated for 18 hours at 37 degrees, 5% CO2. Virus samples were diluted in serum-free DMEM and added to cells after removing serum-containing media. Cells were incubated with virus for 4 hours at 37° C., followed by replacement of media to serum-containing DMEM. Cells were incubated for another 36 hours and harvested by trypsin digestion, followed by neutralization with serum-containing DMEM. Cells were washed once with PBS (5 mM EDTA), passed through a 40 µM cell strainer and analyzed on a FACSCanto II flow cytometer. Data was processed using FlowJo software. Epifluorescent images were taken using a Canon EOS Rebel XS camera adapted to a Zeiss Axiovert 40 CFL.

Molecular Modeling.

The r1c3 capsid model was generated in SWISS MODEL using the crystal structure AAV2 (PDB #1LP3) supplied as a template (Model I) and using the AAV1 (PDB #3NG9), mCherry (PDB #2H5Q), and Red Fluorescent Protein (RFP) (PDB #3NEZ) when a template was not supplied (Model II). Following evaluation of the models in COOT, Model II was selected for further analysis because the two components of the chimera—the AAV2 VP3 and mCherry structures—were consistent with this model. To depict the mCherry insertion, which is in VP1 only, in the context of the capsid, two options were used. One capsid model was generated with a unique AAV2-mCherry pentamer, and the other had five AAV2-mCherry monomers randomly assembled on an AAV2 capsid.

The PAV Lock

Figure 3:
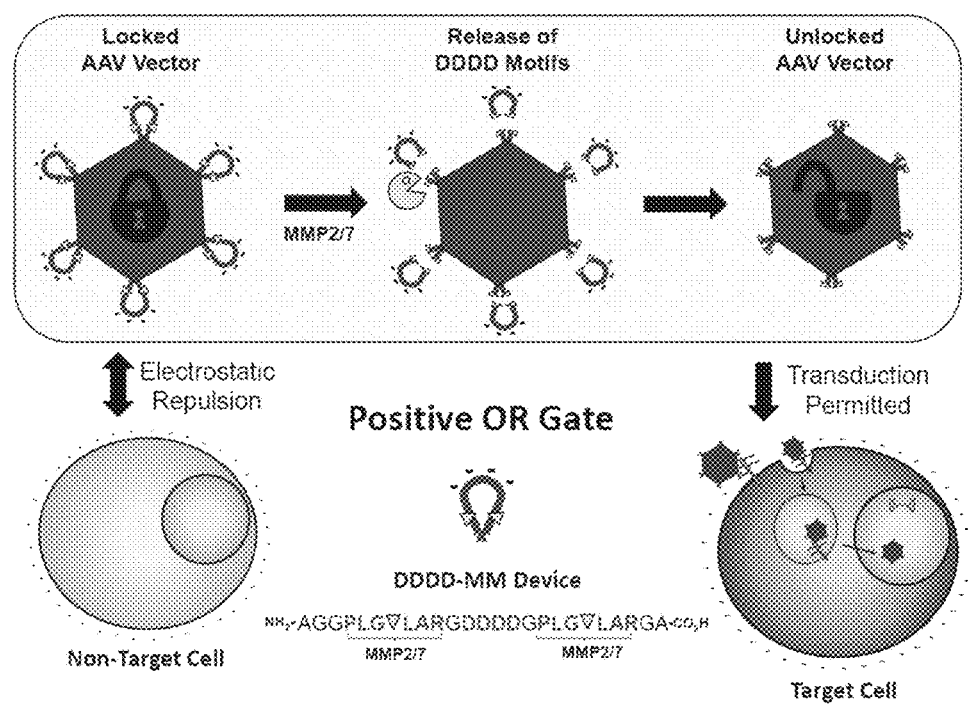
FIG. 3 is a detailed drawing demonstrating one particular embodiment of the peptide lock.
Figure 4:
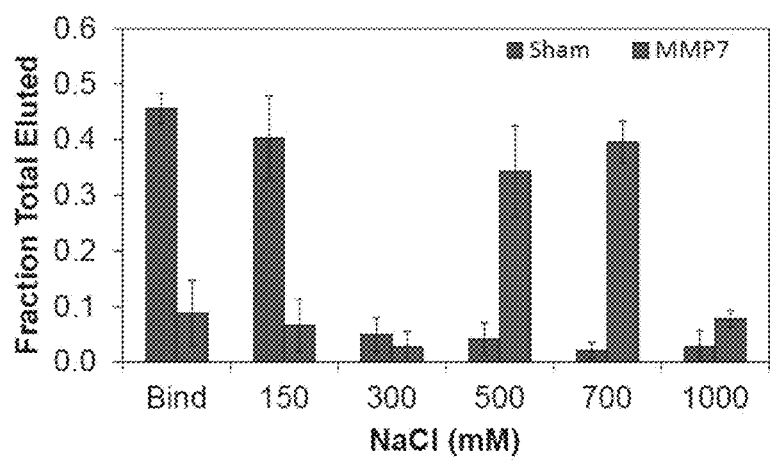
FIG. 4 is a chart depicting heparin binding behavior.
Figure 5:
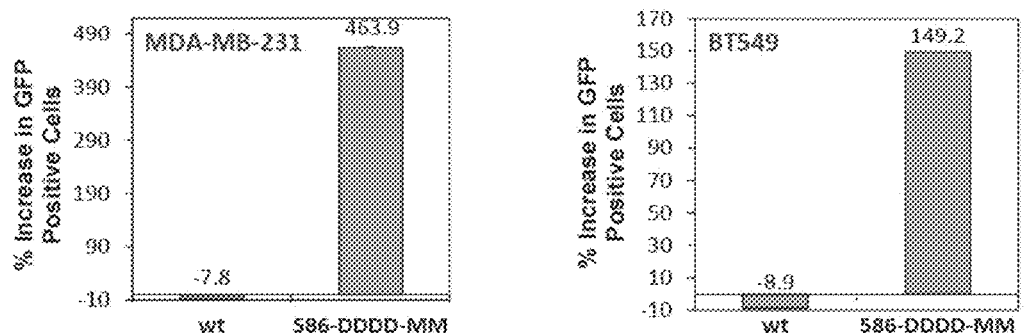
FIGS. 5-7 are charts depicting increases in GFP positive cells.
Figure 6:
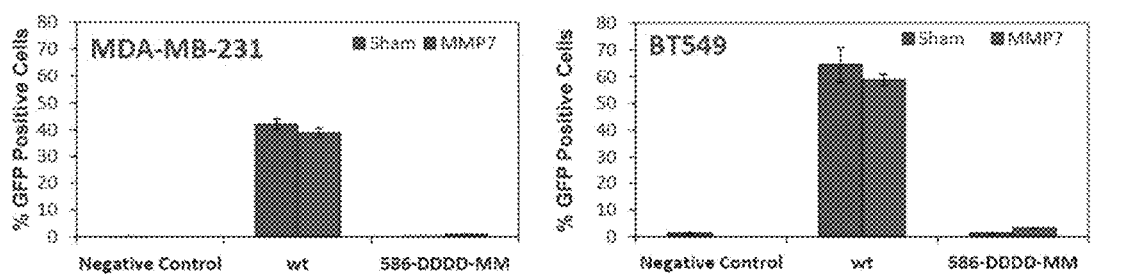
Figure 7:
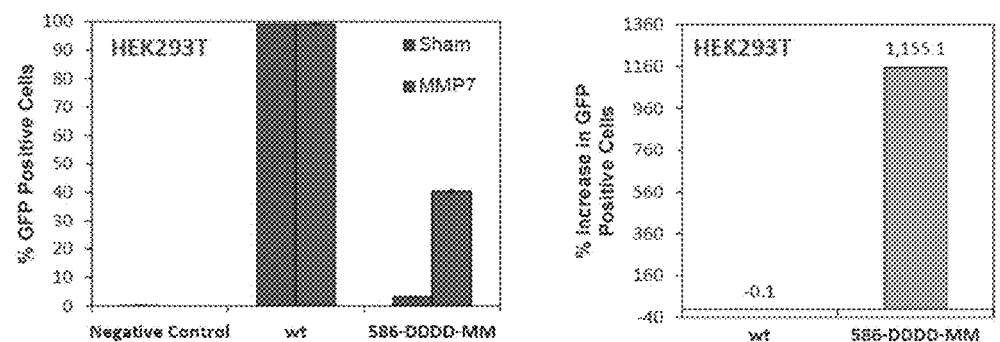

The PAV lock platform we developed, according to certain embodiments, utilizes a tetra-aspartic acid motif ($D_4$), which interferes with electrostatic interactions of negatively charged cell surface glycoproteins, such as HSPGs (FIG. 3). The $D_4$ motif is flanked by proteolytic cleavage motifs, connected by a flexible glycine on each side. The lock contains NgoM IV and Kas I RE sites, which encode small amino acids—glycine and alanine—and make it compatible with the RaPID platform. The lock is designed to be activated by proteases that cleave the susceptible motifs, thus releasing the electrostatic receptor blocking motif, $D_4$.

The lock leaves a few residues on the capsid after cleavage, which may affect receptor binding, depending on their identity, the scissile bond, and the capsid location where the lock is inserted. Thus, careful selection of protease cleavage motifs, linking sequences and other parameters can be used to tune the properties of the PAV lock.

Site Selection.

In order to fulfill the first design criteria, disruption of virus-receptor interactions, the lock must be inserted near the receptor binding domain. In the case of AAV2, the HBD has been mapped to the inter-spike depression at the three-fold axis of symmetry. This domain is a quaternary structure comprised of three sets of intercalating loops from different subunits. Each loop, GH2/3 and GH12/13 are hypervariable regions, and are tolerant to mutation. A sequence alignment of the capsid sequences of homologous serotypes 1-12 illustrates the variability that is tolerated in these loops. Thus, due to their proximity to the HBD and their tolerance to insertional mutagenesis, these loops were chosen as candidate sites for insertion of the PAV lock.

453: Timidity.

The first site we chose to insert the PAV lock was after G453 (453-PAV), at the tip of the outermost spike on the GH2/3 loop. This site was selected because of its potential to fulfill design requirements. Since it lies at the outermost radius of the capsid surface, it is least likely to cause steric hindrance to targeted proteases. Additionally, since G453 hovers just above the heparin binding density, the PAV lock residues that remain after proteolytic cleavage are unlikely to affect receptor binding in the activated PAV. As expected, effective assembly and packaging of the 453-PAV was achieved and the PAV lock was susceptible to cleavage by MMP-7. However, heparin binding was not effectively blocked in the uncleaved state (FIG. 9); thus, the vector was not "locked." Thus, it appears that the 453 site is too distal from the receptor binding pocket in order to modulate receptor binding and the generation of a successful PAV will need a more aggressive approach.

586-PAV: A Working Prototype.

In our second attempt to create a working PAV, we inserted the same PAV lock sequence (FIG. 3) after G586 (586-PAV). Insertion after G586 places the PAV lock into the 3-fold depression between critical heparin binding residues R585 and R588, increasing the likelihood it will disrupt AAV-heparin interactions. Despite the lower elevation of position 586 with respect to the center of the capsid, it remained accessible to cleavage by MMP-7. Additionally, insertion of the PAV lock after G586 resulted in successful ablation of heparin binding, thus creating the first locked PAV prototype.

Remarkably, heparin affinity was restored after cleavage by MMP-7 (FIG. 9). In contrast, the wt virus retained high affinity for heparin, regardless of treatment condition. In order to determine whether the modulation of heparin interactions translates to protease-activatable cell transduction, the enzyme treated 586-PAV, carrying a CMV-GFP transgene, was added to a monolayer of 293T cells. Fluorescence micrographs indicate a striking increase in gene delivery after treatment by MMP-7 compared to a sham control. In order to test whether modulation of heparin binding is responsible for the protease-activated cell transduction, a heparin competition assay was performed (data not shown).

Electrostatics.

Design of the PAV lock uses a $D_4$ motif to block AAV-receptor interactions. Since heparan sulfate exhibits the densest negative charge of any known biomolecule, it is reasonable that disruption of AAV-heparan interactions is influenced by the negative charge of the acidic side chains of the $D_4$ motif. Thus, to test the influence of charge on the operation of the lock, we substituted the $D_4$ motif for uncharged $SG_2S$ (586-PAV-$SG_2S$) and $A_4$ motifs (586-PAV-$A_4$) and positively charged tetra-lysine (586-PAV-$K_4$) (see FIG. 8(a)). Surprisingly, the 586-PAV-$K_4$ was defective in virion assembly and/or packaging. Although 586-PAV-$SG_2S$ and 586-PAV-$A_4$ were more efficient than 586-PAV-$K_4$, genomic titers were still more than a $log_{10}$ fold lower than wt. Preliminary results, indicate that 586-PAV-$A_4$ and 586-$SG_2S$ may have increased heparin binding compared to 586-PAV containing the $D_4$ motif (FIG. 8(b)). These results suggest that the $D_4$ motif does play a role in AAV-heparin interruption, presumably through electrostatic interference.

Clinical Value of PAVs.

In order to demonstrate the utility of PAVs in gene therapy, we tested the protease-activatable gene delivery in several cancer cell lines. Since we expect the activated PAV to behave similarly to AAV2, we selected cell lines that are known exhibit some degree of permissivity to wt AAV2 (FIG. 13). In all cell lines tested—including 2 triple negative breast cancer cell lines, MDA-MB-231 and BT549—we observed a substantial increase in cell transduction. Taken together, these results suggest that the 586-PAV may have real therapeutic value in protease-expressing tumors in vivo.

Targeting Ovarian Cancer In Vivo.

In order to determine utility in vivo, we chose an orthotopic murine ovarian cancer model using on the human HeyA8 ovarian cancer cell line. This model was selected based on the promising in vitro transduction results (FIG. 13).

HeyA8 cells were administered via IP injection and wt or PAV-586 vectors (6e10 VG/mouse, carrying a scCMV-GFP transgene) were injected retro-orbitally after 2.5 weeks (n=5). After 1 week, gene expression was analyzed from harvested tissue via qPCR. The initial results were promising, since we observed that 586-PAV reduced gene expression in the liver by 5-fold (p=0.013) and in the spleen by 3-fold (p=0.086), while increasing tumor expression 13-fold (p=0.072). However, the unexpected 55-fold increase in heart expression is concerning. It is reasonable that the heart transduction by 586-PAV was a result of protease activation in the tumor and subsequent transduction during venous return to the heart. However, when tumor-free mice were injected with the 586-PAV vector, we saw a dominant heart signal consistent with the tumor-bearing mice. Thus, it is unlikely that tumor protease activation played a significant role in heart targeting of 586-PAV.

Specificity and Sensitivity of PAV Prototype.

In order to determine the sensitivity of the prototype PAV, it was treated with various concentrations of MMP-7 and then applied to 293T cells in vitro. The responsive gene expression pattern is determined by the transfer function underlying the 586-PAV device, and is a measure of its sensitivity (FIG. 11). The sensitivity of 586-PAV under these conditions appears to respond to a concentration of MMP-7 between 0.01 and 0.1 nM.

586-PAV: A Selective Bandpass PAV.

PAVs were designed to react to proteases by activation of cell binding in response to lock cleavage. Serendipitously, we discovered an interesting property of our prototype 586-PAV when evaluating its transfer function in response to Cathepsin K (CTSK). As expected, at low concentrations of CTSK, it remains locked. At moderate levels of CTSK, its transduction capability is activated. Strikingly, however at higher concentrations of CTSK, the lock becomes de-activated, presumably by exopeptidolytic removal of residues critical to the HBD. This behavior is reminiscent of a bandpass filter and may have utility in scenarios where it is necessary to activate the vector only in environments containing moderate levels of proteases.

Tuning the Specificity and Sensitivity.

Cleavage Motifs.

Ideally, the specificity of PAV vectors could be altered to match the protease expression profile of the target organ or disease. As a proof of principle, we replaced the 586-PAV cleavage sequences with a motif known to be selective to Cathepsin K (PAV-586-CTSK). PAV-586-CTSK was selective for CTSK, as it could not be activated by saturating levels of MMP-7.

Inherently, sensitivity and specificity are linked attributes in a PAV device, since it is the pattern of sensitivity to different proteolytic enzymes that defines its specificity. To determine if we could use well-characterized substrates from the literature to predictably tune PAV sensitivity/specificity, we constructed a panel of 7 variants with pre-defined substrates (586-PAV-[v1-v7]) (FIG. 8(*a*); FIG. 12). We treated the variants with 100 nM of MMPs 2, 7, and 9 or a sham for 4 hours at 37° C. before applying to 293T cells to analyze transduction efficiency. Predictably, 586-PAV-v1 did not respond to cleavage by MMP-7. But 586-PAV-v2 exhibited specific and saturated transduction upon activation by MMP-7, even though it was not predicted to be specific. 586-PAV-v7 exhibited high transduction efficiency after activation by any MMP tested, which was not far off from the reported kinetic parameters for that substrate.

Surprisingly, cleavage efficiency was highly uncorrelated with the reported specificity constants (kcat/Km). In particular, MMP-2 was often inefficient at cleaving the substrates, even when the specificity constant was reportedly high (compare v2 to v7 in FIG. 12). MMP-7, on the other hand, was slightly more predictable in terms of cleavage efficiency. This difference is likely due to steric hindrance.

Importantly, cleavage of PAVs did not always confer transduction efficiency. However, the PAVs that did exhibit significant transduction capacity consistently contained an arginine at position 6. Thus it seems feasible that this arginine may be important in recreating the HBD after cleavage of the PAV lock.

Linkers.

Defining the selectivity and sensitivity of PAVs will require more than swapping simple pre-defined cleavage sequence. To address the concern of steric hindrance regarding the unpredictable MMP-2 cleavage seen in FIG. 12, we constructed a panel of PAVs containing extra glycines in the linkers connecting the PAV lock with the native capsid sequence for insertions at both 586 and 587. As expected, we found that increasing the glycine linker length increased the cleavage efficiency and transduction ability of both 586- and 587-PAVs by MMP-2. On one hand, these findings may facilitate more predictable engineering of PAVs by increasing the linker lengths. On the other hand, it reveals a potentially useful method to narrow the specificity of a PAV beyond that of the cleavage motif used by shortening the linker length.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A composition comprising an adeno-associated virus and a synthetic peptide, wherein the synthetic peptide is positioned in loop GH2/3 or loop GH12/13 of a capsid of the adeno-associated virus, wherein the synthetic peptide is separate from the capsid in that the capsid does not form any portion of the synthetic peptide, wherein the synthetic peptide comprises a heterologous peptide sequence and an enzymatically processable motif, and wherein the enzymatically processable motif possesses an amino acid sequence that is recognized by a matrix metalloproteinase for cleavage.

2. The composition of claim 1, wherein the heterologous peptide sequence is a tetra-aspartic acid motif ($D_4$).

3. The composition of claim 1, wherein the heterologous peptide sequence has low affinity for host cell surface receptors.

4. The composition of claim 1, wherein the synthetic peptide further comprises a linker amino acid sequence separating the heterologous peptide sequence from the enzymatically processable motif.

5. The composition of claim 4, wherein the linker amino acid sequence is selected from the group consisting of AG, GA, G, GGGGS (SEQ ID NO: 2), and combinations thereof.

6. The composition of claim 1, wherein the synthetic peptide comprises AG-PLGLAR-G-DDDD-G-PLGLAR-GA (SEQ ID NO: 3).

7. The composition of claim 1, wherein the synthetic peptide is in loop GH12/13.

8. The composition of claim 1, wherein the synthetic peptide comprises AG-IPESLRAG-G-DDDD-G-IPESL-RAG-GA (SEQ ID NO: 5).

9. The composition of claim 1, wherein the synthetic peptide comprises AG-IPVSLRSG-G-DDDD-G-IPVSL-RSG-GA (SEQ ID NO: 6).

10. A composition comprising an adeno-associated virus having a synthetic peptide, wherein the synthetic peptide is genetically encoded into a capsid of the adeno-associated virus so as to be at least partially exposed to the surface of the capsid, wherein the synthetic peptide blocks biologically active domains on the surface of the capsid, and wherein the synthetic peptide is comprised of a tetra-aspartic acid motif ($D_4$).

11. The composition of claim 1, wherein the enzymatically processable motif is PLGLAR (SEQ ID NO: 1).

12. The composition of claim 1, wherein the synthetic peptide further comprises an additional enzymatically processable motif.

13. The composition of claim 1, wherein the synthetic peptide further comprises an additional enzymatically processable motif, wherein the additional enzymatically processable motif is HPGGPQ (SEQ ID NO: 8).

14. The composition of claim 1, wherein the enzymatically processable motif is HPGGPQ (SEQ ID NO: 8).

15. The composition of claim 14, wherein the synthetic peptide further comprises an additional enzymatically processable motif.

16. The composition of claim 15, wherein the heterologous peptide sequence is positioned between the enzymatically processable motif and the additional enzymatically processable motif.

17. A composition comprising an adeno-associated virus having a synthetic peptide, wherein the synthetic peptide is at least partially exposed to the surface of the adeno-associated virus to block biologically active domains thereon, and wherein the synthetic peptide comprises a heterologous peptide sequence, a linker amino acid sequence, and an enzymatically processable motif, wherein the linker amino acid sequence separates the heterologous peptide sequence from the enzymatically processable motif, and wherein the linker amino acid sequence is selected from the group consisting of AG, GA, G, GGGGS (SEQ ID NO: 2), and combinations thereof.

18. The composition of claim 17, wherein the enzymatically processable motif is susceptible to cleavage by a matrix metalloproteinase.

19. The composition of claim 17, wherein the enzymatically processable motif has the amino acid sequence set forth in SEQ ID NO: 1.

20. The composition of claim 17, further comprising an additional enzymatically processable motif, wherein the heterologous peptide sequence is flanked on one side by the enzymatically processable motif and on the other side by the additional enzymatically processable motif.

21. The composition of claim 20, wherein the synthetic peptide has the amino acid sequence set forth in SEQ ID NO: 7.

22. The composition of claim 1, wherein the synthetic peptide is positioned in loop GH2/3.

* * * * *